US006380170B1

(12) United States Patent
Müller et al.

(10) Patent No.: US 6,380,170 B1
(45) Date of Patent: Apr. 30, 2002

(54) NUCLEIC ACID CONSTRUCT FOR THE CELL CYCLE REGULATED EXPRESSION OF STRUCTURAL GENES

(75) Inventors: Rolf Müller; Ningshu Liu; Jörk Zwicker; Hans-Harald Sedlacek, all of Marburg (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/025,343

(22) Filed: Feb. 18, 1998

(30) Foreign Application Priority Data

Feb. 18, 1997 (EP) .............................. 97102547

(51) Int. Cl.$^7$ ............................................. A61K 48/00
(52) U.S. Cl. ...................... 514/44; 424/93.2; 435/320.1; 435/325; 435/455; 536/23.1; 536/24.1
(58) Field of Search ............................ 435/320.1, 455; 514/44; 424/93.2; 536/23.1, 24.1

(56) References Cited

U.S. PATENT DOCUMENTS

| 5,830,880 A | 11/1998 | Sedlacek et al. ............... 514/44 |
| 5,854,019 A | 12/1998 | Sedlacek et al. ............ 435/69.1 |
| 5,885,833 A | 3/1999 | Mueller et al. .............. 435/372 |
| 5,916,803 A | 6/1999 | Sedlacek et al. ......... 435/320.1 |

FOREIGN PATENT DOCUMENTS

| FR | 2735789 | 12/1996 |
| WO | 95/16774 | 6/1995 |
| WO | 96/06938 | 3/1996 |
| WO | 96/25494 | 8/1996 |

OTHER PUBLICATIONS

Anderson et al., Nature, vol. 392, 25–30, 1998.*
Verma et al. (Nature, vol. 389, 18, pp. 239–242), 1997.*
F. Ehlert et al., "Cell cycle–regulated transcription of the human cdc25c gene is controlled by a novel regulatory element", British Journal of Haematology, vol. 87, Supp. 1, 1994, Abstract 483.
N. Liu et al., "Nucleic Acids Research", vol. 24, No. 15, *Cell cycle–regulated repression of B–myb transcription: cooperation of an E2F site with a contiguous corepressor element*, pp. 2905–2910, (1996).
J. Zwicker et al., "Nucleic Acids Research", vol. 23, No. 19, *Cell cycle regulation of cdc25C transcription is mediated by the periodic repression of the glutamine–rich activators NF–Y and Sp1*, pp. 3822–3830, (1995).
J. Zwicker et al., "The EMBO Journal", vol. 14, No. 18, *Cell cycle regulation of the cyclin A, cdc25C and cdc2 genes is based on a common mechanism of transcriptional repression*, pp. 4514–4522, (1995).
J. Zwicker et al, "Science", vol. 271, *Cell Cycle Regulation of E2F Site Occupation in Vivo*, pp. 1595–1597, (Mar. 15, 1996).

S.J. Weintraub et al., "Nature" 358, *Retinoblastoma protein switches the E2F site from positive to negative element*, pp. 259–261, (Jul. 16, 1992).
K. Helin et al., "Trends in Cell Biology" 3,*The retinoblastoma protein as a transcriptional repressor*, pp. 43–46, (Feb. 3, 1993).
M. Zamanian et al., "Molecular Biology of the Cell" 4, *Transcriptional Repression by the Rb–Related Protein p107*, pp. 389–396, (Apr. 1993).
R. Mueller, "TIG" 11(5), *Transcriptional regulation during the mammalian cell cycle*, pp. 173–178, (May 1995).
J.R. Nevins, "Science" 258, *E2F: A Link Between the Rb Tumor Suppressor Protein and Viral Oncoproteins*, pp. 424–429, (Oct. 16, 1992).
N.B. La Thangue, "Biochemical Society Transactions" 24, *E2F and the molecular mechanisms of early cell–cycle control*, 6 pages, (1996).
J.A. DeCaprio et al., "Proc. Natl. Acad. Sci, USA" 89, *The retinoblastoma–susceptibility gene product becomes phosphorylated in multiple stages during cell cycle entry and progression*,pp. 1795–1798,(Mar. 1992).
R. Fagan et al., "Cell" 78, *Phosphorylation of E2F–1 Modulates its interaction with the Retinoblastoma Gene Product and the Adenoviral E4 19 kDa Protein*, pp. 799–811, (Sep. 9, 1994).
M. Hatakeyama et al, "Genes & Development" 8, *Collaboration of $G_1$ cyclins in the functional inactivation of the retinoblastoma protein*, pp. 1759–1771, (1994).
R.A. Weinberg, "Cell" 81, *The Retinoblastoma Protein and Cell Cycle Control*, pp. 323–330, (May 5, 1995).
D.G. Johnson et al., "Genes & Development" 8, *Autoregulatory control of E2F1 expression in response to positive and negative regulators of cell cycle progression*, pp. 1514–1525, (1994).
K. Ohtani et al, "Molecular and Cellular Biology" 16(12), *Expression of the HsOrc1 Gene, a Human ORC1 Homolog, Is Regulated by Cell Proliferation via the E2F Transcription Factor*, pp. 6977–6984, (Dec. 1996).
E.W.F. Lam et al., "The EMBO Journal" 12(7), *An E2F–binding site mediates cell–cycle regulated repression of mouse B–myb transcription*, pp. 2705–2713, (1993).
E.W.F. Lam et al., "The EMBO Journal" 13(4), *HPV16 E7 oncoprotein deregulates B–myb expression: correlation with targeting of p107/E2F complexes*, pp. 871–878, (1994).

(List continued on next page.)

*Primary Examiner*—Dave T. Nguyen
(74) *Attorney, Agent, or Firm*—Heller Ehrman White and McAuliffe

(57) ABSTRACT

The invention refers to a nucleic acid construct comprising at least one activator sequence, at least one chimeric promoter module comprising a nucleotide sequence which binds a protein of the E2F family and a protein of the CDF-1 family, and at least one gene, wherein said chimeric promoter module promotes expression of the gene in the cell cycle later than the B-myb promoter but earlier than the cdc25C promoter. The invention also concerns the purification and identification of CDF-1 protein, and use of this protein to develop new control systems.

16 Claims, 2 Drawing Sheets

OTHER PUBLICATIONS

E.W.F. Lam et al., "Gene" 160, *Cell–cycle regulation of human B–myb transcription*, pp. 277–281, (1995).

KM Hsiao et al., "Genes & Development" 8, *Multiple DNA elements are required for the growth regulation of mouse E2F1 promoter*, pp. 1526–1537, (1994).

L. Zhu et al., "Molecular and Cellular Biology" 15(7), *Differential Roles of Two Tandem E2F Sites in Repression of the Human p107 Promoter by Retinoblastoma and p107 Proteins*, pp. 3552–3562, (Jul. 1995).

F. Oswald et al., "Molecular and Cellular Biology" 16(5), *The E2F Transcription Factor Activates a Replication–Dependent Human H2A Gene in Early S Phase of the Cell Cycle*, pp. 1889–1895, (May 1996).

J. Zwicker et al., "Science" 271, *Cell Cycle Regulation of E2F Site Occupation in Vivo*, pp. 1595–1597, (Mar. 15, 1996).

J. Zwicker et al., "The EMBO Journal" 14(18), *Cell cycle regulation of the cyclin A, cdc25C and cdc2 genes is based on a common mechanism of transcriptional repression*, pp. 4515–4522, (1995).

N. Liu, et al., "Nucleic Acids Research" 24(15), *Cell cycle–regulated repression of B–myb transcription: cooperation of an E2F site with a contiguous corepressor element*, pp. 2905–2910, (1996).

J.D. Dignam et al., "Nucleic Acids Research" 11(5), *Accurate transcription initiation by RNA polymerase II in a soluble extract from isolated mammalian nuclei*, pp. 1475–1489, (1983).

M.P. Hay et al., "Drugs of the Future" 21(9), *Antibody–directed enzyme–prodrug therapy (ADEPT)*, pp. 917–931, (1996).

M. Truss et al., "Endocrine Reviews" 14(4), *Steroid Hormone Receptors: Interatin with Deoxyribonucleic Acid and Transcription Factors*, pp. 459–479, (Aug. 1993).

M. Cross et al., "Cell" 64, *Growth Factors in Develpment Transformation, and Tumorigenesis*, pp. 271–280, (Jan. 25, 1991).

G.L. Semenza et al., "Proc. Natl. Acad. Sci. USA" 88, *Hypoxia–inducible nuclear factors bind to an enhancer element located 3' to human erythropoietin gene*, pp. 5680–5684, (Jul. 1991).

M.W. McBurney et al., "Nucleic Acids Research" 19(20), *The mouse Pgk–1 gene promoter contains an upstream activator sequence*, pp. 5755–5761, (Sep. 23, 1991).

F.C. Lucibello et al., "The EMBO Journal" 14(1), *Periodic cdc25C transcription is mediated by a novel cell cycle–regulated repressor element (CDE)*, pp. 132–142, (1995).

J.D. Bennett et al., "Oncogene" 13, *E2F binding is required but not sufficient for repression of B–myb transcription in quiescent fibroblasts*, pp. 1073–1082, (1996).

* cited by examiner

Figure 1:

| mutations constructs | -16 | -15 | -14 | -13 | -12 | -11 | -10 | -9 | -8 | -7 | -6 | -5 | -4 | -3 | -2 | -1 | +1 | +2 | relative activity |
|---|---|---|---|---|---|---|---|---|---|---|---|---|---|---|---|---|---|---|---|
| cdc25c (wt) | G | G | C | G | G | A | A | G | G | G | T | T | G | A | A | G | G | T | 8.4 |
| -1/+2 | | | | | | | | | | | | | | | | T | G | T | 8 |
| -2/+2 | | | | | | | | | | | | | | | C | G | G | T | 1.3 |
| -6/-3 | | | | | | | | | | | G | | T | C | | | | | 1.9 |
| -10/-7 | | | | | | | C | | T | T | G | | | | | | | | 3 |
| -2 | | | | | | | | | | | | | | | - | | | | 2.3 |
| -4 | | | | | | | | | | | | | - | | | | | | 1.2 |
| -6 | | | | | | | | | | | - | | | | | | | | 1.4 |
| -7 | | | | | | | | | | - | | | | | | | | | 1.8 |
| -8 | | | | | | | | | - | | | | | | | | | | 7.8 |
| -9 | | | | | | | | - | | | | | | | | | | | 6.9 |

Figure 2:

| | 1 | E2F motif / CDF-1 motif | 2 | 3 | 4 | 5 | Repression | Half-maximal transcription (hrs) | CDF-1 binding | DP/E2F binding |
|---|---|---|---|---|---|---|---|---|---|---|
| B-myb | ACTT | GGCGG | GA | GA | TAGGAA | AGT | + | 8 | ± | ++ |
| cdc25C | GGCT | GGCGG (CDE) | AA | GG | TTGAA (CHR) | TGG | + | 13 | ++ | - |
| B-C1 | C | | B | B | B | B | + | 8.5 | ± | + |
| B-C1,2 | C | | C | B | B | B | - | - | ± | - |
| B-C2 | B | | C | B | B | B | nd | nd | nd | - |
| B-C4 | B | | B | B | C | B | + | →11 | ++ | ++ |
| C-B1 | B | | C | C | C | C | + | 13 | ++ | - |
| C-B1,2 | B | | B | C | C | C | + | →10.5 | ++ | ++ |
| C-B4 | C | | C | C | B | C | - | - | - | - |
| C-B3,4 | C | | C | B | B | C | - | - | - | nd |
| C-B3,4,5 | C | | C | B | B | B | - | - | ± | nd |
| C-B4,5 | C | | C | C | B | B | nd | nd | ± | nd |

NUCLEIC ACID CONSTRUCT FOR THE CELL CYCLE REGULATED EXPRESSION OF STRUCTURAL GENES

FIELD OF THE INVENTION

The invention relates to nucleic acid constructs that comprise at least one activator sequence, at least one promoter sequence and at least one regulated gene. The as:, invention also relates to repressors that are involved in cell-cycle regulation.

BACKGROUND OF THE INVENTION

One of the factors implicated in cell cycle-regulated repression is E2F, which can form DNA-binding repressor complexes through its interaction with pocket proteins, such as pRb (Weintraub et al., Nature 358, 259 (1992); Helin and Harlow, Trends Cell Biol. 3, 43 (1993); Zamanian and La Thangue, Mol. Biol. Cell 4, 389 (1993)).

E2F is a heterodimeric transcription factor composed of members of the E2F and DP multi-gene families (Nevins, Science 258, 424 (1992); Müller, Trends Genet. 11, 173 (1995); La Thangue, Transactions 24, 54 (1996)). Another transcription factor belonging to the E2F gene family is e.g. E2F-5 (WO 96/25494). Transcriptional activation by E2F is modulated during the cell cycle by pocket proteins of the pRb family. E2F is repressed in $G_0$ and early $G_1$, but during cell cycle progression both DP/E2F moiety and the associated pocket proteins are hyperphosphorylated by $G_1$-specific cyclin dependent kinases leading to the dissociation of the inhibitory ternary complex (DeCaprio et al., Proc. Natl. Acad. Sci. USA 89, 1795 (1992); Fagan et al., Cell 78, 799 (1994); Hatakeyama et al., Genes Dev. 8, 1759 (1994); Weinberg, Cell 81, 323 (1995)). This dissociation generates transcriptionally active "free E2F" and leads to the activation of E2F-regulated genes. Therefore, e.g. a vector comprising a nucleic acid encoding an E2F regulator and/or E1A regulator has been already used to transfect a differentiated neuron inducing DNA synthesis (WO 95/16774).

Among the promoters controlled by transcriptional repression through E2FBSs are E2F-1, orc-1 and B-myb (Lam and Watson, EMBO J. 12, 2705 (1993); Hsiao et al., Genes Dev. 8424, 1526 (1994); Johnson et al., Genes Dev. 8424, 1514 (1994); Ohtani et al., Mol. Cell. Biol. 16, 6977 (1996)). The role of E2F, however, is not exclusively activating. This has first been demonstrated for the mouse B-myb gene (Lam and Watson, EMBO J. 12, 2705 (1993); Lam et al., EMBO J. 13, 871 (1994); Lam et al., Gene 160, 277 (1995); Zwicker et al., Science 271, 1595 (1996)). Mutation of the E2F binding site (E2FBS) in the B-myb promoter leads to a dramatically increased activity selectively in $G_0$ and consequently to a loss of cell cycle regulation.

Other examples in this context are the E2F, p107, histone H2A and orc1 promoters, where mutations of E2FBSs also abrogate repression and cell cycle regulation (Hsiao et al., Genes Dev. 8424, 1526 (1994); Johnson et al., Genes Dev. 8424, 1514 (1994); Zhu et al., Mol. Cell. Biol. 15, 3552 (1995); Ohtani et al., Mol. Cell. Biol. 16, 6977 (1996); Oswald et al., Mol. Cell. Biol. 16, 1889 (1996)).

The identification of several genes that are repressed through E2FBSs suggests that E2F-mediated transcriptional repression is a frequent mechanism of cell cycle regulated transcription. However, the mechanism of B-myb gene repression deviates from all models proposed for the action of E2F in that it requires a second element located directly downstream of the E2FBS (Bennet et al., Oncogene 13, 1073 (1996); Zwicker et al., Science 271, 1595 (1996)). In addition, occupation in the cell of the B-myb E2FBS is cell cycle-regulated and is seen only during phases of repression (Zwicker et al., Science 271, 1595 (1996)). These observations are very similar to those made with other promoters, such as cdc25C, cdc2 and cyclin A, which are periodically repressed through two cooperating elements, the E2FBS-like CDE and the adjacent CHR (Zwicker et al., EMBO J. 14, 4514 (1995)).

The mechanism of cell. cycle regulated transcription was discovered through the analysis of genes that are expressed at later stages of the cell cycle. When the cdc25C promoter, which is up-regulated in late $S/G_2$, was studied by in vivo footprinting and mutational analysis, a novel repressor element, the "cell cycle dependent element" (CDE), was identified (Lucibello et al., EMBO J. 14, 132 (1995)). The CDE is occupied in $G_0$–$G_1$ and its occupation is lost in $G_2$, when cdc25C is expressed.

That CDE mediated repression plays a role in regulating other promoters as well was shown by the presence of functional CDEs in the cyclin A and cdc2 promoters which are derepressed in late $G_1/S$ (Zwicker et al., EMBO J. 14, 4514 (1995)). These studies also led to the discovery of an additional element contiguous with the CDE, which is identical in all three promoters. This element was termed "cell cycle genes homology region" (CHR) (Zwicker et al., EMBO J. 14, 4514 (1995)).

Mutation of either the CDE or the CHR in the cdc25C, cdc2 or cyclin A promoter largely abolishes repression in $G_2$. These functional data were supported by the demonstration of $G_0$–$G_1$-specific protein binding to both the CDE and CHR in genomic footprinting. Interestingly, CDE contacts the major groove of DNA while binding to CHR occurs in the minor groove (Zwicker et al., EMBO J. 14, 4514 (1995)). The nucleotide sequence of the CDE-CHR and its use for diagnosis, screening and gene therapy has already been claimed in WO 96/06943.

The discovery that the CHR cooperates with a CDE in the repression of promoters and the identification of CHR-like sequences adjacent to the E2FBS in the B-myb promoter, prompted detailed investigations into the mechanism of B-myb repression. These studies showed that the CHR-like region is indispensable for repression and acts as a co-repressor element together with the E2FBS (Bennett et al., Oncogene 13, 1073 (1996)). This region has been termed Bmyb-CHR (Bennett et al., Oncogene 13, 1073 (1996)) or DRS (Bennett et al., Oncogene 13, 1073 (1996)).

In addition, genomic footprinting clearly showed a loss of E2F site occupation paralleling the derepression of B-myb in mid-$G_1$ (Zwicker et al., Science 271, 1595 (1996)). These observations showed that E2F-CHR sites regulate transcription of genes induced in late $G_1$, in a similar way as CDE-CHR sites lead to derepression of genes in S or $G_2$. In addition, these findings indicate that repressing E2F sites differ from activating E2F sites by the absence of a contiguous CHR corepressor element. Taken together, both E2F- and CDE-mediated repression, acting at different stages in the cell cycle, are dependent on promoter-specific CHR elements (Liu, N. et al., Nucleic Acids Res. 24, 2905, No. 15 (1996)).

The CDE is identical to E2FBS core sequences, such as those in the B-myb promoter (GGCGG) (Zwicker et al., EMBO J. 14, 4514 (1995)), but it remains elusive what determines the distinction of an E2FBS from a CDE. In addition, CDE or CDE-CHR binding activities have not been identified to date and the relationship of CDE binding factor(s) to the E2F family of transcription factors is unclear.

Both repressor modules repress activating sequences, located upstream of E2FBS-Bmyb-CHR or CDE-CHR. The Bmyb-CHR element inhibits an upstream activator sequence in the early phase ($G_0$ to mid $G_1$ phase), and the CDE-CHR to a later phase ($G_0$ to S phase) of the cell cycle.

This finding led to the construction of genes that contain a noncell-specific, cell-specific, virus-specific and/or metabolic-specific activator sequence, cell cycle-specific promoter modules like CDE-CHR or E2FBS-Bmyb-CHR controlling the activation of the activator sequence, and a gene encoding a therapeutic protein.

Such gene constructs have been claimed for gene therapy of various diseases (see e.g. WO 96/06943; D196.05274.2; D196.17851.7; WO 96/06940; WO 96/06938; WO 96/06941; WO 96/06939). However, constructs having various characteristics are desired for optimum control of gene expression. Thus, the need remains for new nucleic acid constructs with differing cell-cycle dependent gene expression.

SUMMARY OF THE INVENTION

The inventors surprisingly found that the factors involved in repression of the B-myb regulated promoter are different from factors involved in repression of CDE-CHR regulated promoters. Upon further study, the inventors found a new binding factor that interacts with CDE-CHR regulated promoters, and identified a regulatory sequence associated with this control mechanism. From this discovery, the inventors designed nucleic acid constructs useful for controlling gene expression in a cell-cycle dependent manner.

Thus, in one embodiment, the invention relates to a nucleic acid construct comprising at least one activator sequence; at least one chimeric promoter module comprising a nucleotide sequence which binds a protein of the E2F family and binds a CDF-1 protein; and at least one gene, wherein said chimeric promoter module promotes expression of said gene.

In another embodiment, the invention relates to a process for the preparation of a three-part nucleic acid construct, said nucleic acid construct comprising at least one activator sequence; at least one chimeric promoter module comprising a nucleotide sequence which binds a protein of the E2F family and binds a CDF-1 protein; and at least one gene, said process comprising ligating the three parts together.

In yet another embodiment, the invention relates to CDF-1 protein produced by a process comprising preparing a nuclear extract from HeLa cells; and purifying this extract by affinity chromatography in the presence of an oligonucleotide comprising a CDE-CHR sequence motif.

In a further embodiment, the invention relates to a process of identifying an unknown material or molecule as containing CDF-1 inhibition or stimulation activity, comprising providing CDF-1 to a solution, in vitro or in vivo, that contains a nucleic acid construct, said construct comprising at least one activator sequence; at least one chimeric promoter module comprising a nucleotide sequence which binds a protein of the E2F family and binds a CDF-1 protein; and at least one gene, providing said unknown material or molecule to said solution; and determining the effect of adding the material to expression of said gene.

BRIEF DESCRIPTION OF THE FIGURES

FIG. 1 presents a structure-function analysis of the cdc25C CHR (SEQ ID NO:14). Promoter construct cdc25C (based on C290; Zwicker et al., EMBO J. 14, 4514 (1995)) mutations in the CHR region were analyzed for their effects on cell cycle regulation in NIH3T3 cells. Positions −16 to −12 represent the CDE defined previously (Zwicker et al., EMBO J. 14, 4514 (1995)). Results of transient luciferase assays are expressed as the ratio of RLUs observed with growing cells relative to the activity in quiescent cells. The results shown in the figure summarize the data of 4 independent experiments using at least two independent preparations of plasmid DNA. Values represent averages; in all cases standard deviations were not higher than ±1.5. An SV40 reporter plasmid was included in each experiment to standardize the factor of induction (the SV40 reporter typically gave a 1.5-fold higher value in growing compared to quiescent cells).

FIG. 2 shows the effects of specific nucleotide exchanges between the B-myb E2FBS-CHR module (SEQ ID NO:15) and the cdc25C CDE-CHR motif (SEQ ID NO:16) on cell cycle regulation and DNA binding of E2F and CDF-1 complexes. The B-myb and cdc25C repressor modules are shown at the top. Five positions where the sequences differ from each other are designated regions 1–5. Each of the mutants indicated below harbors specific exchanges between the two promoters in a B-myb (upper block) or cdc25C (lower block) promoter background. The letters "B" and "C" indicate whether a particular mutant contains cdc25C (C) or B-myb (B) nucleotides in regions 1–5 (e.g., B-C1 is a B-myb sequence containing the cdc25C nucleotides in region 1).

DETAILED DESCRIPTION

The inventors discovered that the B-myb gene was repressed through E2F complexes in conjunction with a CHR-binding factor, while the cdc25C promoter was repressed by a novel activity that was characterized and is termed herein as CDE-CHR binding factor-1 ("CDF-1"). The inventors analyzed the interaction of CDF-1 with repressor elements from several cell cycle-regulated genes. Using in vivo and in vitro DMS footprinting, and EMSA and functional assays of promoter luciferase constructs, the inventors identified the following characteristic CDF-1 activities.

(a) CDF-1 interacts in a cooperative fashion with both CDE and CHR in the cdc25C promoter, in agreement with CHR-dependent occupation of CDE observed in a cell system.

(b) CDF-1 interacts with G residues in the CDE (major groove) and with A residues in the CHR (minor groove). This protection pattern is identical to the one found by in vivo footprinting (Zwicker et al., EMBO J. 14, 4514 (1995)).

(c) The binding of CDF-1 to sequences containing mutated CDE or CHR motifs correlates precisely with the function of such mutated elements in cell cycle regulated repression.

(d) CDF-1 binds with similar efficiency to all known CDE-CHR regulated promoters, i.e., cdc25C, cdc2 and cyclin A, but only weakly to B-myb.

(e) CDF-1 was found to bind CDE-CHR containing promoters of the cdc25C, cdc2 and cyclin A genes with similarly high affinity while interaction with the B-myb promoter E2FBS-CHR module was comparably weak.

(f) E2F cannot mediate repression via the cdc25C CDE-CHR element and, vice versa, CDF-1 is unable to mediate repression via E2FBS-Bmyb-CHR.

CDF-1 protein was isolated from nuclear extracts from HeLa suspension cultures by high salt extraction and subsequent purification by affinity chromatography in the presence of CDE-CHR sequence motifs. For purposes of this disclosure, "CDF-1" protein refers to a protein which binds to CDE-CHR sequence motifs and may refer to any of a number of proteins that share this characteristic. Thus, "a CDF-1" refers to any of such proteins which share the 6 characteristic CDF-1 activities enumerated above and which identify a CDF-1 family of proteins.

Hence, a first embodiment of the present invention concerns a CDF-1 protein that may be obtained by the following steps:

(a) preparing a nuclear extract from HeLa cells, and
(b) purifying the extract of step (a) by affinity chromatography in the presence of an oligonucleotide containing a CDE-CHR sequence motif, in particular in the presence of a motif containing the sequence (SEQ ID NO:11) GGCTG GCGGA AGGTT TGAAT, or a tandem sequence such as (SEQ ID NO: 12) GGCTG GCGGA AGGTT TGAAT GGCTG GCGGA AGGTT TGAAT.

In a particularly preferred embodiment the oligonucleotide containing the CDE-CHR sequence motif is coupled to agarose, e.g. through streptavidin. In general, the nuclear extract according to step (a) is prepared by salt extraction of HeLa cells, in particular by high salt extraction e.g. according to Dignam, J. D. (1983) Nucleic Acids Res., 11, 1475–1489. The CDF-1 protein can be eluted from the chromatography column by step-wise increased salt concentration, e.g. by increasing the salt concentration of KCl up to 1M.

The CDF-1 protein is in particular useful for the identification of inhibitors or stimulators of CDF-1, in particular of the repressor function of CDF-1. As such, this protein may be used to develop new strategies and materials for controlling gene expression.

Another result of the isolation and functional characterization of CDF-1 was the identification of nucleotides that are essential for binding and repressor function of E2F/DP and CDF-1.

In general, the binding was dependent on the presence of intact versions of CDE and CHR. The consensus sequence of the CDE was defined as G/CGC/TGG/C (GGCGG in cdc25C; Zwicker al., EMBO J. 14, 4514 (1995)) and the CHR sequence of cdc25C as the sequence TTTGAA. In contrast to the nucleotides in this region the nucleotides between the CDE and the CHR (AAGG, see FIGS. 1, 2) and the nucleotides downstream from the CHR (TGG, see FIGS. 1, 2) can be altered without detectable effects on repressor function.

A similar binding site-specific interaction pattern was observed with partially purified CDF-1.

Nucleotides in the E2FBS: of B-myb and the CDE of cdc25C that are responsible for discriminating between E2F and CDF-1 binding are the nucleotides directly adjacent to the E2FBS/CDE core (GGCGG). Thus, the two nucleotides up-stream (CT in B-myb) and one nucleotide down-stream (G in B-myb) generally cause E2F binding, but not CDF-1 binding. Based on these findings it was possible to assay the function of a mutant B-myb promoter with a strongly reduced E2F binding but normal CDF-1 interaction, and to show that repression of this construct is impaired. This data shows that the interaction with E2F is in general essential, and that the binding of CDF-1 is insufficient to confer any cell cycle regulation on the B-myb promoter.

The situation is very much different for the CDE-CHR repressed cdc25C promoter. In this case, no binding of E2F is found, and the strong interaction with CDF-1 is generally dependent on the CHR. Thus, the E2F binding site is larger (i.e., at least 9 nucleotides) than the 5-nucleotide CDE (Zwicker al., EMBO J. 14, 4514 (1995)), but does not include the CHR, while the CDF-1 binding site consists of the 5-nucleotide CDE and the contiguous 6-nucleotide CHR. It was therefore possible to create promoters which possess the ability to interact with both E2F and CDF-1 with high efficiency either by changing the Bmyb-CHR to a cdc25C CHR (B-C4 see FIG. 2) or by changing the cdc25C CDE flanking nucleotides to their B-myb counterparts (see FIG. 2, C-B1,2). Interestingly, these promoters showed novel properties with respect to the timing of derepressing during the cell cycle, in that half-maximal activity was observed later than with B-myb but earlier than with cdc25C, i.e., in early mid S-phase. These observations show that the differential binding of E2F and CDF-1 contribute to the timing of regulation. In agreement with this observation it was found that a B-myb promoter mutant showing preferential and strong CDF-1 binding (see FIG. 2, B-C1,3,4) shows cdc25C-like expression kinetics.

Therefore, another embodiment of the present invention is a nucleic acid construct comprising:

a) at least one activator sequence,
b) at least one chimeric promoter module comprising a nucleotide sequence which binds a protein of the E2F family and a CDF-1 protein; and
c) at least one gene, wherein said chimeric promoter module causes an up-regulation of gene expression in the cell cycle later than the B-myb promoter but earlier than the cdc25C promoter.

In a preferred embodiment the activator sequence is located upstream of the chimeric promoter module.

It has been found that the E2FBS-Bmyb-CHR promoter module of the B-myb gene (positions of mutations underlined) (SEQ ID NO: 13) ACTTGGCGGGAGATAGGAAA, (Zwicker et al., Science 271:1595 (1996)) mutated to ACTTGGCGG-GAGATTTGAAT (SEQ ID NO.: 1) comprises a high-affinity E2F as well as a CDF-1 binding site. The binding of E2F as well as of CDF-1 to this nucleotide sequence in vivo (within the cell) is confined to the $G_0$ and $G_1$ phases and is undetectable in the S, $G_2$ and M phase and the nucleotide SEQ ID NO.: 1 is strongly able to repress in the $G_0$ and $G_1$ phase of the cell cycle the activity of an activator sequence (located upstream of SEQ ID NO.: 1) to activate the transcription of a gene (located downstream of SEQ ID NO.: 1).

It has likewise been found that the CDE-CHR promoter module of the cdc25C gene (positions of mutations underlined) (SEQ ID NO:11) GGCTGGCGGAAG-GTTTGAAT (EMBO J. 14, 4514 (1995)) mutated to GCT-TGGCGGGAGGTTTGAAT (SEQ ID NO.: 2) comprises a high-affinity CDF-1 as well as E2F binding site. The binding of CDF-1 as well as E2F to this nucleotide sequence in vivo is confined to the $G_0$ and $G_1$ phases and is undetectable in the S, G and M phase and the nucleotide SEQ ID NO.: 2 is strongly able to repress in the $G_0$ and $G_1$ phase of the cell cycle the activity of an activator sequence (located up-stream of SEQ ID NO.: 2) to activate the transcription of a gene (located downstream of SEQ ID NO.: 2).

Therefore, a preferred embodiment of the present invention refers to a nucleic acid construct with a chimeric promoter module comprising at least one nucleotide sequence which is selected from the group consisting of ACTTGGCGGGAGATTTGAAT (SEQ. ID NO.: 1) and GCTTGGCGGGAGGTTTGAAT (SEQ ID NO.: 2).

In general, the promoter module interacts with the activator sequence, and said interaction affects expression of the gene.

The activator generally functions by way of a non-specific, cell-specific, virus-specific and/or metabolic-specific activation of basal transcription. The gene is generally expressed in a cell-cycle specific, in a cell-specific and cell cycle-dependent, in a virus-specific and cell-cycle dependent and/or in a metabolic-specific and cell-cycle dependent manner.

A nucleic acid construct according to the present invention preferably consists of DNA. The term "nucleic acid construct", as used herein, means an artificial nucleic acid structure which can be transcribed in the target cells. Such a construct may be inserted into a vector. Nonviral vectors such as plasmid vectors or viral vectors may be used. The kind of vectors and the technique of insertion of the nucleic acid construct according to this invention is known to the artisan. A nucleic acid construct according to the invention does not occur in nature in the arrangement described by the present invention. In other words, the gene of the nucleic acid construct is not naturally combined with the activator sequence and the chimeric promoter module.

Another embodiment of the present invention refers to a cell comprising a nucleic acid construct or a vector of the present invention.

A nucleic acid construct according to the invention allows a gene to undergo cell-cycle specific expression or both cell- and cell cycle-specific expression, or virus- and cell cycle-specific or metabolic- and cell cycle-specific expression. In one preferred embodiment, the gene codes for a pharmacologically active substance. In another preferred embodiment, the gene encodes an enzyme which cleaves an inactive precursor of a pharmaceutical into an active pharmaceutical ("prodrug" into drug). Examples of such pharmaceutical precursor to pharmaceuticals are described by Sedlacek et al., Contrib. to Oncol. 43, Karger Verlag (1992); Hay et al., Drugs of the Future 21, 917 (1996).

An "activator sequence", denotes a nucleotide sequence which is part of a gene and which can activate expression of a gene. This activation can occur by virtue of binding regulatory protein, also known as "transcription factors" which, as a result of this binding, activate transcription of a gene located downstream. The regions referred to as "downstream" sequences are those located in the direction of transcription, whereas sequences arranged in the opposite direction are referred to as "upstream" sequences.

In one embodiment of the present invention, the activator sequence may be non-specific, cell-specific or virus-specific or metabolic-specific. As used in this specification, "cell-specific" means that the activator sequence is selected from a gene coding for a protein that is specifically expressed in a given cell and "virus-specific" means that the activator sequence is selected from a viral gene; metabolic-specific means, that the activator sequence is selected from a gene, coding for a protein, that is specifically expressed under defined metabolic conditions. Thus, in another preferred embodiment, the activator sequence is selected from the group of promoters or enhancers which activate transcription in endothelial cells, serosal cells, smooth muscle cells, muscle cells, synovial cells, hemopoietic cells, macrophages, lymphocytes, leukemia cells, tumor cells, or keratinocyte cells, glial cells, or from promoter sequences or enhancer sequences of the viruses HBV, HCV, HSV, HPV, EBV, HTLV, CMV, SV40, or HIV.

Examples of cell-specific, virus-specific and metabolic-specific activator sequences are described in WO 96/06940; WO 96/06938; WO 96/06941 and WO 96/05994. The activator sequence can be a promoter or enhancer.

A chimeric promoter module according to this invention comprises a binding site for a protein of the E2F family as well as CDF-1. Examples for such promoter modules are SEQ ID NO.: 1 and SEQ ID NO.: 2. The chimeric promoter module "cooperates" with the activator sequence because both promoter module and activator sequence coordinately promote, i.e. cause an increase, in expression of the gene under their control.

In one preferred embodiment of this invention this chimeric promoter module is located downstream of the activating sequence.

In another preferred embodiment of this invention the promoter module may be combined with an activator sequence according to the technology described in D196.17851.7. In this patent application several examples are described for combining several promoters. One example is an activator responsive promoter unit. It consists of two different activator subunits A and B. The expression products of A and B fuse together and thereby form a transcription factor activating an activator responsive promoter. The expression of activator subunits A and B is under the control of a promoter for A and a promoter for B. These promoters may be identical or different.

In another preferred embodiment of this invention, the chimeric promoter module may be combined with a second promoter to be selected from a series of promoters, comprising strong nonspecifically activable promoters such as promoter of RNA polymerase III, promoter of RNA polymerase II, CMV promoter and enhancer and/or SV40 promoter; or a viral promoter and/or activator sequence such as the activator sequence of HBV, HCV, HSV, HPV, EBV, HTLV and/or HIV; or metabolically activatable promoter or enhancer sequences, e.g., an enhancer or promoter inducible by hypoxia; or another cell-cycle specific promoter, e.g., the promoter of the cdc25C gene, cyclin A gene, cdc2 gene, the B-myb gene, the DHFR-gene or the E2F-1 gene; or a tretracyclin activatable promoter, e.g., the tetracyclin operator in combination with the corresponding repressor; or a cell-specific activatable promoter; to those promoters belong upstream activating sequences of such genes that encode for proteins expressed predominantly or exclusively in the selected cell type.

The nucleic acid constructs of the present invention can be used in genetic engineering and, in particular, in gene therapy.

In gene therapy, genes which are intended to be expressed in the body are introduced into the body. Regulation of the expression of these genes is important for the therapeutic effect of gene therapy. The present invention therefore relates also to nucleic acid constructs which can be used in gene therapy. Techniques for gene therapy are well known to the skilled artisan. For example, WO93/24640 and WO95/11984 disclose methods and compositions for in vivo gene therapy with a nonviral or viral vector technology. In another example, WO95/06743 discloses a method whereby therapeutic nucleic acid constructs are introduced into a patient's isolated airway epithelial cells via transformation with a viral (AAV) vector containing a construct. The transformed cells are then administered to the patient. In addition, FR 2735789 discloses pharmaceutical compositions containing a recombinant adenovirus.

The technology for the various nonviral vectors that can be used as carriers for the constructs of this invention and applied to cells in vitro or injected or applied in vivo to patients are likewise well. known to the skilled artisan.

In one preferred embodiment, the nucleic acid construct can be used for cell-specific and cell cycle-regulated expression of at least one gene. In another preferred embodiment, the nucleic acid construct can be used for virus-specific and cell cycle-regulated expression of at least one gene. In still another preferred embodiment, the nucleic acid construct can be used for a metabolic specific and cell cycle-regulated expression of at least one gene.

The nucleic acid construct or the cell according to the present invention, is preferably used in the treatment of a disorder which is characterized by or associated with cell proliferation. Such treatment comprises, for example, introduction of said nucleic acid construct into a target cell.

Examples of disorders, characterized by or associated with cell proliferation are tumor diseases, leukemias, cardiovascular diseases, inflammatory reactions, autoimmune reactions, allergies, arthritis, psoriasis, impending rejection of transplanted organs, CNS damages, infectious diseases, blood clotting disorders and chronic viral infections. Such diseases can be treated by systemic or local application of the constructs or cells of the present invention. Expression of such constructs in the respective proliferative cell population can be controlled by the cell-specific, metabolic-specific or virus-specific activator sequence and the cell cycle-specific promoter module. The expression product of the construct of invention can directly or indirectly inhibit cell proliferation or kill the proliferating cells.

By virtue of the structure of the construct, it may be expressed during the stage of cell proliferation.

For treatment of other disorders, the activator sequence and the gene encoding an active substance, in the nucleic acid constructs or cells according to the present invention are selected depending on the purpose of use.

In general, the gene encodes a substance which is selected from the group consisting of a cytokine, a growth factor, a cytokine receptor, a growth factor receptor, a protein having an antiproliferative effect, a protein having an apoptotic effect, a protein having a cytostatic effect, a protein having a cytotoxic effect, a protein having an inflammatory effect, a protein having an antiinflammatory effect, a protein having an immunosuppressive effect, an antibody, an antibody fragment, an angiogenesis inhibitor, a coagulation factor, a fibrinolytic compound and an anticoagulant, a blood protein, a viral antigen, a bacterial antigen and a tumor antigen and a fusion protein between a ligand such as a growth factor, cytokine or antibody and one of the afore mentioned substances.

In this regard, the invention comprises the following constructs and therapeutic methods.

1. Therapy of Tumors and Chronic Inflammations via Inhibition of Endothelial Cell Proliferation Tumors as well as chronic inflammations are characterized by the formation of new blood vessels by proliferating endothelial cells. In one embodiment, such proliferating endothelial cells are the target cells to be transduced by the constructs of the invention to express a protein that directly or indirectly inhibits the proliferation of endothelial cells and/or kills proliferating endothelial cells and adjacent tumor cells.

1.1 Activator Sequences Activated in Endothelial Cells

In one embodiment, activator sequences activated in endothelial cells include those gene-regulatory sequences and elements from promoters for genes which encode for proteins that are detectable in particular in endothelial cells. Examples of these endothelial cells-specific proteins and the promoter sequences of their genes are described in WO 96/06940.

To those promoters belong promoter or activator sequences of genes encoding the brain-specific endothelial glucose-1 transporter, Endoglin, VEGF receptor-1 (flt-1), VEGF receptor-2 (flk-1, KDR), tie-1 or tie-2, B61 receptor (Eck-receptor), B61, Endothelin, e.g., Endothelin B or Endothelin-1, Endothelin receptor, especially the Endothelin B receptor, Mannose-6-phosphat receptors, von Willebrand factor, IL-1α, IL-1β, IL-1 receptor, vascular cell adhesion molecule (VCAM-1), synthetic activator sequences, e.g., activator sequences comprising and/or 5'-TTATCT-3' binding the transcription factor GATA-2.

1.2 Activator Sequences Activated in Cell Adjacent to Activated Endothelial Cells When endothelial cells are proliferating, adjacent cells become accessible to macromolecules from the blood due to "tight junctions". These functional and anatomic interrelations allow cells in the vicinity of activated endothelial cells to act as target cells for the purpose of this invention. Examples of activator sequences being activated in adjacent cells are described in WO96/06940.

To those activator sequences or promoters belong promoters or activator sequences of genes encoding for VEGF. The gene regulatory sequences for the VEGF gene are the 5' flanking region or the 3' flanking region or the c-Src gene or the v-Src gene.

Other examples are steroid hormone receptors and their promoter elements (Truss and Beato, Enocrin. Rev. 14, 459 (1993)), especially the mouse mammary tumor virus promoter.

1.3 Genes for Antitumor or Antiinflammatory Activity Substances

An "antiinflammatory" substance may have one or more of the following characteristics: inhibition of endothelial cell proliferation, inhibition of angiogenesis, formulation of thrombi, cytostatic or cytotoxic properties, ability to induce apoptosis or the ability to convert a prodrug into an active drug with cytotoxic, cytostatic or antiinflammatory properties. As used in this application, an "antitumor" substance may have one or more of the preceding properties. In addition, an "antitumor" substance may be a substance that induces inflammation. Examples of these substances and their genes are described in WO96/06940, WO96/06941 and D19617851.7.

Genes encoding those substances are for example genes for inhibitors of cell proliferation, e.g. for the retinoblastoma protein (pRb=p110) or the related p107 and p130 protein, the p53 protein, the p21 (WAF-1) protein, the p16 protein, other cdk-inhibitors, the GADD45 protein or the bak protein. The retinoblastoma protein (pRb=110) and related p107 and p130 proteins are inactivated by phosphorylation; preferred are such genes of these cell-cycle inhibitors that contain mutations for the inactivation sites of the expressed proteins, but without impairing the function of these inhibitors.

Other examples are genes of thrombosis inducing factors and/or inhibitors of angiogenesis, e.g. for plasminogen activator inhibitor-1 (PAI-1), PAI-2, PAI-3, angiostatin, interferones, e.g., IFNα, IFNβ, IFNγ, platelet factor 4, IL-12, TIMP-1, TIMP-2, TIMP-3, leukemia inhibitory factor (LIF) or tissue factor (TF) and its active fragments.

Further examples are structual genes for cytostatic or cytotoxic proteins, e.g., for perforin, granzym, IL-2, IL-4, IL-12, interferones, e.g., IFNα, IFNβ, IFN-γ, TNF, TNFα, TNFβ, oncostatin M, sphingomyelinase or magainin and magainin derivatives.

1.4 Genes for Cytostatic or Cytotoxic Antibodies, Antibody Fragments and for Fusion Proteins Between Antigen Binding Antibodies or Antibody Fragments and Cytostatic, Cyotoxic or Inflammatory Proteins or Enzymes Cytostatic or cytotoxic antibodies include those directed against membrane structures on endothelial cells or on tumor or leukemia cells. Such antibodies were described for example by Sedlacek et al., Contrib. to Oncol. 32, Karger Verlag, München (1988) und Contrib. to Oncol. 43, Karger Verlag, München (1992). Other examples are antibodies specific for Sialyl Lewis, peptides on tumors that are recognized by T-lymphocytes, proteins expressed by oncogenes, gangliosides, e.g., GD3, GD2, GM, 9-0-acetly GD3, fucosyl GM1, blood group antigens and their precursors, antigens on polymorphic epithelial mucin, antigens on heat shock proteins or CD13, CD15, CD33, CAMAL, CD5, CD1c, CD23, idiotypes and isotypes of membrane immunoglobulines, CD33, M38, IL-2 receptors, T-cell receptors, CALLA, CD19 or Non-Hodgkin lymphoma.

1.5 Genes for Fusion Proteins Between Target Cell Binding Ligands and Cytostatic or Cytotoxic Proteins or Enzymes Ligands include all proteins that bind to the cell membrane of endothelial cells, e.g., growth factors or fragments of growth factors like PDGF, bFGF, VEGF, TGFβ. Moreover, to such ligands belong adhesion molecules that bind to activated and/or proliferating endothelial cells, e.g., Slex, LFA-1, MAC-1, LECAM-1, VLA-4 or vitronectin. Moreover, to such ligands belong compounds that bind to the cell membrane or membrane receptors of tumor or leukemia cells, e.g., growth factors or fragments of growth factors. Such growth factors were already described by Cross et al., Cell 64, 271 (1991), Aulitzky et al., Drugs 48, 667 (1994), Moore, Clin. Cancer Res. 1, 3 (1995), Van Kooten et al., Leuk. Lymph. 12, 27 (1993)).

1.6 Genes for Inducers of Inflammation

Genes for inducing inflammation include, for example, RANTES (MCP-2), monocyte chemotactic and activating factor (MCAF), IL-8, macrophage inflammatory protein-1 (MIP-1, -β), neutrophil activating protein-2 (NAP-2), IL-3, IL-5, human leukemia inhibitory factor (LIF), L-7, IL-11, IL-13, GM-CSF, G-CSF, M-CSF, Cobra venom factor (CVF) or sequences of CVF that functionally correspond to human complement factor C3b, human complement factor C3 or sequences of C3b, cleavage products of human complement factors C3 that are functionally and structurally similar to CVF or bacterial proteins that activate complement or induce inflammations, e.g., porins of *Salmonella typhimurium*, "clumping" factors of *Staphylococcus aureus*, modulins of gram-negative bacteria, "major outer membrane protein" of legionella or of haemophilius influenza type B or of Klebsiella, and M-molecules of Streptococcus group G.

1.7 Genes for Enzymes that Convert a Prodrug into a Drug

Genes that encode enzymes that can convert or cleave prodrugs into active cytostatics include, for example genes for enzymes such as Herpes simplex virus thymidinkinase, varizella zoster virus thymidinkinase, bacterial nitroreductase, bacterial β-glucuronidase, β-glucuronidase of Secale cereale, human β-glucuronidase, human carboxy peptidase (CB), e.g., CB-A of mast cells, CB-B of pancreas, bacterial carboxy peptidase, bacterial β-lactamase, bacterial cytosine deaminase, phosphatase, e.g., human alkaline phosphatase, human acid prostata phosphatase, type 5 acid phosphatase, oxidase, e.g., human lysyl oxidase, human acid D-amino oxidase, peroxidase, e.g., human gluthatione peroxidase, human eosinophil peroxidase, human thyroidyl peroxidase and galactosidase.

2. Active Substance for Remedying Deficient Production of Blood Cells 2.1 Selection of an Activator Sequence for Hemopoietic Cells The activator sequence used for hemapoietic cells may be a gene-regulatory sequence or an element of a gene which encodes a protein which is expressed particularly strongly or selectively in hemopoietic cells. Gene-regulatory sequences of this type include promoter sequences for genes of a cytokine or its receptor, the expression of which in immature hemopoietic cells or in adjacent cells such as, for example, the stroma cells of the bone marrow, precedes the subsequent cytokine which acts on the hemopoietic cells and is required as active substance. Cytokines of this type which act on immature hemopoietic cells are, for example, such as stem cell factor, IL-1, IL-3, IL-6, GM-CSF or thrombocytopoietin or receptors for these cytokines. References for such cytokines are given in WO96/0694 1. To these activator sequences belong the promoter sequence of the gene of e.g. stem cell factor receptor, stem cell facor, IL-1α, IL-1 receptor, IL-3, IL-3 receptor (α-subunit), IL-3 receptor (β-subunit), IL-6, IL-6 receptor, GM-CSF, GM-CSF receptor (α-chain), interferon regulatory factor 1 (IRF-1), erythropoietin or erythropoietin receptor.

In another embodiment, the activator sequence may be metabolic specific. Examples of metabolic (i.e., by hypoxia) activatable activator sequences were described by Semenza et al., PNAS 88, 5680 (1991) or Mc Burney et al., Nucl. Acids Res. 19, 5755 (1991).

2.2 Selection of the Genes for Active Substance for Hemopoietic Cells

An "active substance for hemopoietic cells" generally means a protein that effects proliferation and/or differentiation of blood cells. Examples of genes for such a substance are listed in WO96/06941. To these belong genes for the therapy of anaemia, e.g. for erythropoietin, genes for the therapy of leukopenia, e.g. for G-CSF, GM-CSF, genes for the therapy of thrombocytopenia, e.g. for IL-3, leukemia inhibitory factor (LIF), IL-11 or thrombopoietin.

3. Active Substance for the Therapy of Autoimmune Diseases, Allergies, Inflammations and to Prevent Organ Rejections 3.1 Selection of the Activator Sequence The activator sequences which may be used are the promoter sequences of genes strongly activated in macrophages or lymphocytes or of genes for proteins which are extensively produced during the immune response in macrophages and/or in lymphocytes. Examples of promoter sequences of genes encoding such proteins are described in WO96/06941. To these proteins belong IL-1 receptor, IL-1α, IL-1β, IL-2, IL-2 receptor, IL-3, IL-3 receptor (α-subunit), IL-3 receptor (β-subunit), IL-4, IL-4 receptor, IL-5, IL-6, interferon regulatory factor 1 (IRF-1), IFN responsive promoter, IL-7, IL-8, IL-10, IL-11, IFN, GM-CSF, GM-CSF receptor (α-chain), IL-13, LIF, macrophage colony stimulating factor (M-CSF) receptor, type I and II macrophage scavenger receptors, MAC-1 (leukocyte function antigen), LFA-1α (leukocyte function antigen), and p150,95 (leukocyte function antigen).

3.2 Selection of Genes Encoding Active Substances

An "active substance" for purposes of the invention may be a DNA sequence for a cytokine, a chemokine, a growth factor or one of their inhibitors, the extracellular portion of a receptor for a cytokine or growth factor, an antibody, an antibody fragment, or an enzyme inhibitor or an enzyme. The choice of the active substance depends on the basic disorder to be treated and the promoter sequence selected. Representative examples are a gene appropriate for treatment of an autoimmune disease, allergy, inflammation or for prevention of organ rejection as described in WO96/06941. To these examples belong, for example, genes for therapy of allergies, for example, those that encode IFNβ, IFNγ, IL-10, antibodies or antibody fragments specific for IL-4, soluble IL-4 receptors, IL-12, and TGFβ.

Genes to prevent rejection of transplanted organs, e.g. encode for IL-10, TGFβ, soluble IL-1 receptors, soluble IL-2 receptors, IL-1 receptor antagonists, soluble IL-6 receptors, immune suppressive antibodies or fragments containing $V_H$ and $V_L$ fragments of these antibodies or $V_H$- and $V_L$ fragments conjugated by a linker. Antibodies are specific for T-cell receptor or its CD3 complex, against CD4 or CD8, against IL-2 receptor, IL-1 receptor or IL-4 receptor or against the adhesion molecules CD2, LFA-1, CD28 or CD40.

Genes for the therapy of antibody-mediated autoimmune diseases, e.g., encode for, TGFβ, IFNα, IFNβ, IFNγ, IL-12, soluble IL-4 receptors, soluble IL-6 receptors or immune suppressive antibodies or their $V_H$ and $V_L$ containing fragments.

Genes for the therapy of cell-mediated autoimmune diseases, e.g. encode for IL-6, IL-9, IL-10, IL-13, TNFα, IL-4, TNFβ, immune suppressive antibodies, and $V_H$ or $V_L$ containing fragments of antibodies.

Genes that encode inhibitors of cell proliferation, cytostatic or cytotoxic proteins, or enzymes for the conversion or activation of prodrugs into cytostatics, or fusion proteins may be the same as genes for tumor therapy.

4. Active Substance for the Treatment of Arthritis 4.1 Selection of the Activator Sequence for Arthritis The activator sequence generally means a promoter or enhancer sequence with which transcription factors are formed or actively interact in e.g. synovial cells and inflammatory cells. For the purpose of this invention, the preferred promoter sequences include gene-regulatory sequences and elements from genes which code for proteins that are particularly expressed in synovial cells and inflammatory cells. Examples of such proteins are given in WO96/06941. To these proteins belong e.g. MMP-1 (interstitial collagenase), MMP-3 (stromelysin/transin) and tissue inhibitors of metallo proieinases (TIMP), e.g., TIMP-1, TIMP-2 or TIMP-3.

4.2 Selection of Genes for Active Substances Related to Arthritis

An "active substance" for this purpose generally means a DNA sequence whose expressed protein directly or indirectly inhibits inflammation, for example in the joint, and/or promotes reconstitution of extracellular matrix such as cartilage and/or connective tissue in the joint. Examples of such proteins are given in WO96/06941. To these proteins belong e.g. IL-1 receptor antagonist, soluble IL-1 receptor, IL-6, soluble TNF receptor, IL-4, IL-10, insulin-like growth factor, TGFβ, superoxiddismutase or TIMP, e.g., TIMP-1, TIMP-2 or TIMP-3

5. Antiinfective Substance

In general, the active substance can be prepared in two fundamentally different forms: for the therapy of viral infections and invasions by parasites or for the prophylaxis of infectious diseases due to viruses, bacteria or parasites. Vaccines are generally used for the prophylaxis of infectious diseases. However, the possibilities for preparing effective vaccines by conventional means are limited. Thus, the technology of DNA vaccines has been developed. However, these DNA vaccines give rise to questions about safety and side effects (Fynan et al., Int. J. Immunopharm. 17, 79 (1995); Donnelly et al., Immunol. 2, 20 (1994)). The following constructs for the therapy and prophylaxis of infectious diseases are distinguishable from prior art substances because of their cell specificity and cell cycle regulation that provides a high degree of safety of these substances:

5.1 Selection of the Activator Sequence 5.1.1 Therapy of Infectious Diseases

An activator sequence which may be chosen for the therapy of infectious diseases comprises promoter sequences from cellular genes whose activity is altered in particular by infections with bacteria or parasites, or the promoter sequences to be chosen are those from viruses which transform the cells infected by them and stimulate proliferation. These viruses include, for example, HBV, HCV, HSV, HPV, HIV, EBV and HTLV. Examples for those activator sequences are described in WO96/06941.

5.1.2 Prophylaxis of Infectious Diseases

An activator sequence which may be chosen for the prophylaxis of infectious disease comprises a promoter sequence that is generally strongly activated in endothelial cells, muscle cells, lymphocytes or macrophages or that belongs to cellular genes coding for proteins that are generally highly expressed in endothelial cells, muscle cells, macrophages or lymphocytes.

Examples of activating sequences are given in the preceeding and subsequent sections.

5.2 Selection of Genes for Active Substances 5.2.1 Therapy of Infectious Diseases An active substance which may be selected is the DNA for a protein which has cytostatic, cytotoxic, antibacterial or antiviral effects or which may be an enzyme that transforms the inactive precursor into a cytostatic, cytotoxic, antibacterial or antiviral drug. Examples of cytotoxic or cytostatic proteins and of cytokines and growth factors with antiviral activity are described in WO96/06941. To these substances belong for example antiviral active cytokines and growth factors, e.g., IFNα, IFNβ, IFN-γ, TNFβ, TNFα, IL-1 or TGFβ. Other examples are antibodies that inactivate a specific virus or VH and VL containing fragments hereof or their VH and VL fragments conjugated by a linker. Examples of antiviral antibodies are antibodies specific for HBV, HCV, HSV, HPV, HIV, EBV, HTLV, Coxsackie virus or Hantaan virus. Further examples are a rev. binding protein, e.g., RBP9-27, RBP1-8U, RBP1-8D or pseudogene of RBP1-8.

To these substances belong also e.g. a ribozyme that catalyses the mRNA of genes for cell-cycle control proteins or the mRNA of a respective virus or gene for antibacterial proteins, e.g., antibodies that neutralize bacterial toxins or that opsonize bacteria, e.g., antibodies specific for meningococcus C or B, *E. coli,* borrelia, pseudomonas, *Helicobacter pylori* or *Staphylococcus aureus.*

Antibodies or antibody fragments are exemplary antibacterial or antiviral proteins. As noted above, for some substances, enzymatic conversion of a precursor to the active form may be required. In such case, the antibacterial, antiviral, cytotoxic, or antiparasitic substance is added after a construct according to the invention has already been administered. Examples for enzymes converting such prodrugs and the genes for such enzymes were described in WO96/06940 and WO96/06941 and in the preceeding section.

5.2.2 Prophylaxis of Infectious Diseases

In one embodiment, the active substance may be an antibody or an antibody fragment specific for the pathogen. In another embodiment, the active substance may be a protein which is formed by the pathogen and which leads, through an immune response, i.e. by antibody binding and/or by cytotoxic lymphocytes, to neutralization and/or killing of the pathogen. Neutralizing antigens of this type are already in use as immunizing antigens (see review by Ellis, Adv. Exp. Med. Biol. 327, 263 (1992)). DNA sequences encoding such proteins are used to make constructs according to the invention. Examples of those genes are described in WO96/06941, e.g., genes coding for influenza A virus antigen, HIV antigens, rabies virus antigen, HSV (Herpes simplex virus) antigen, RSV (respiratory syncytial virus) antigen, parainfluenza virus antigen, rotavirus antigen, VZV (varizella zoster virus) antigen, CMV (cytomegalo virus) antigen, measles virus antigen, HPV (human papilloma virus) antigen, HBV (hepatitis B virus) antigen, HCV (hepatitis C virus) antigen, HDV (hepatitis D virus) antigen, HEV (hepatitis E virus) antigen, HAV (hepatitis A virus) antigen, vibrio cholera antigen, borrelia Burgdorferi antigen, *Helicobacter pylori* antigen, malaria antigen and an antiidiotype antibody or its antibody binding fragments, the complementary determining regions of which are copies of the protein or carbohydrate structure of the neutralization antigen of the infectious organism.

6. Active Substance for the Treatment of Leukemias and Tumors 6.1 Selection of an Activator Sequence for Leukemias and Tumors An activator sequence may be a promoter or enhancer sequence with which transcription factors formed or active in leukemia cells or tumor cells interact. However, for the purpose of this invention preferred activator sequences include gene-regulatory sequences and elements of genes which encode for proteins formed in particular in tumor cells or leukemia cells. Examples are cited in WO96/06941, e.g., promoters of genes encoding for c-myc, HPS-70, bcl-1/cyclin D-1, bcl-2, IL-6, IL-10, NFα, TNFβ, HOX-11, BCR-Abl, E2A-PBX-1, PML-RATA (promyelocytic leukemia-retinoic acid receptor), c-myc, N-CAM-proteins, hepatitis growth factor receptor, L-plastin or polymorphic epethelial mucin (PEM).

6.2 Selection of the Genes for Active Substances for Leukemias and Tumor Cells

The active substance for this purpose generally means a protein that inhibits the proliferation of cells, in particular also of tumor cells or leukemia cells. These inhibitors of cell proliferation include, for example, the DNA sequences for inhibitory, cytostatic, apoptotic and cytotoxic proteins and enzymes for cleavage of prodrugs that have already been described.

An inhibitor of cell proliferation furthermore means a DNA sequence which expresses a protein which has, directly or indirectly, a cytostatic or cytotoxic effect on leukemias or tumors. Such proteins have already been described in the preceding sections. DNA sequences encoding such proteins may be used to make constructs according to the present invention.

An inhibitor of cell proliferation furthermore generally means a DNA sequence encoding for protein or peptide that induces a humoral or cellular immune response cytotoxic or cytostatic for the tumor. To such proteins or peptides belong e.g. genes for tumor vaccines. Hereto belong antigens on tumor cells. For example such antigens were reviewed by Sedlacek et al., Contrib. to Oncol. 32, Karger Verlag, München (1988) and Contrib. to Oncol. 43, Karger Verlag, München (1992). Additional examples are antigens or the genes coding for Sialyl Lewis, peptides on tumor cells recognizable by T-cells, proteins expressed by oncogenes, blood group antigens and their precursors, antigens of the polymorphic epithelial mucin and antigens of the heat shock proteins.

7. Active Substance for Inhibiting Smooth Muscle Cell Proliferation in Vascular Occlusions 7.1 Selection of an Activator Sequence for Smooth Muscle Cells In one embodiment, the activator sequences may be gene-regulatory sequences or elements of genes which encode proteins that are particularly formed in smooth muscle cells. Examples of promoters for genes encoding such proteins are described in WO96/06938 and WO96/06940. To these belong tropomyosin, α-actin, α-myosin, receptor for PDGF, receptor for FGF, MRF-4, phosphofructokinase A, troponin C, myogenin, receptors for endothelin A, desmin, VEGF and artificial promoters.

Furthermore, factors of the Helix-Loop-Helix (HLH) family (MyoD, Myf-5, myogens MRF4) and the Zinkfinger protein GATA-4 are described as muscle-specific transcription activators. HLH proteins as well as GATA-4 show muscle-specific transcription not only with promoters of muscle-specific genes but also in a heterologous context, e.g., with artificial promoters. Such artificial promoters are for example: multiple copies of (e.g., 4×) 5'-AGCAGGTGTTGGGAGGC-3' (SEQ ID NO.: 3) or multiple copies of 5'-GGCCGATGGGCAGAT AGAGGGGGCCGATGGGCAGATAGAGG-3' (SEQ ID NO.: 4).

7.2 Selection of Genes for Active Substances of Smooth Muscle Cells

The active substance for this purpose generally means a protein that inhibits the proliferation of smooth muscle cells. Examples of these inhibitors of proliferation were described in the preceding sections.

8. Active Substance for Inhibiting or Activating Coagulation 8.1 Selection of an Activator Sequence for Inhibiting or Activating Coagulation Activator sequences useful for this purpose generally may be gene-regulatory sequences or elements of genes which encode proteins detectable in smooth muscle cells, in activated endothelial cells, in activated macrophages or in activated lymphocytes.

8.1.1 Smooth Muscle Cells

Examples of promoter sequences for genes in smooth muscle cells are mentioned in WO96/06938 and in the preceding section.

8.1.2 Activated Endothelial Cells or Cells Adjacent to Activated Endothelial Cells Examples of proteins which are formed particularly in activated endothelial cells are described in WO96/06938 and WO96/06940 and in the preceding sections.

8.1.3 Activated Macrophages and/or Activated Lymphocytes

An activator sequence for this purpose generally means a promoter sequence from a gene encoding a protein which is formed extensively during an immune response in macrophages and/or in lymphocytes. Examples are described in WO96/06941, WO96/06938 and in the preceding sections.

8.2 Selection of Genes for Active Substances for Inhibiting or Activating Coagulation or for Modulating a Cardiovascular System In one embodiment, the active substance to be used for this purpose is a protein which inhibits, directly or indirectly, platelet aggregation or a coagulation factor, or stimulates fibrinolysis. Thus, an active substance of this type is referred to as an anticoagulant. The anticoagulants to be employed are genes for, for example, plasminogen activators (PA), for example tissue PA (tPA) or urokinase-like PA (uPA) or hybrids of tPA and uPA or protein C, antithrombin III, C-1S inhibitor, α1 antitrypsin, the tissue factor pathway inhibitor (TFPI) or hirudin.

In another embodiment, the active substance to be used for this purpose is a protein which promotes blood coagulation. Examples of such proteins are, for example, blood plasma proteins such as factor VIII, factor IX, von Willebrand factor, F XIII, PAI-1 or PAI-2.

In a third embodiment the active substance to be used for this purpose is a protein that modulates the cardiovascular system by inducing angiogenesis or by lowering blood pressure. Examples of genes encoding such proteins are angiogenesis factors, e.g., VEGF and FGF, and peptides for lowering blood pressure, e.g., kallikrein and endothelial cell "nitric oxide synthase".

In an additional embodiment the active substance to be used for this purpose is a gene encoding a blood protein. Examples of such blood proteins are albumin, C1-inactivator, serum cholinesterase, transferrin, and 1-antitrypsin.

9. Active Substance for Protecting from CNS Damage 9.1 Activator Sequences for an Active Substance for Protecting from CNS Damage 9.1.1 Activator Sequences Activated in Endothelial Cells In one embodiment, this type of activator includes promoter sequences for genes of proteins specific to endothelial cells. Examples of these promoter sequences are given in WO96/06939 and are described in preceding sections.

9.1.2 Activator Sequences Activated in Glial Cells

One preferred activator sequence is a promoter or enhancer sequence with which transcription factors formed or active to a particular extent in glial cells interact. Examples of these activator sequences are provided in WO96/06939. To these belong promoters of genes encoding the Schwann cell-specific protein periaxin, glutaminesynthetase, the glial cell-specific protein (glial fibrillary acidic protein=GFAP), the glial cell protein S100b, IL-6 (CNTF), 5-HT-receptor, TNFα, IL-10, insulin-like growth factor receptor I and II, and VEGF.

9.2 Choice of Genes for Neurospecific Factors

A "neurospecific factor" for the purpose of the present invention may be a DNA sequence which encodes a neuronal growth factor or an inhibitor or suppressor of TNFα. Examples of these genes are provided in WO96/06939. To these belong genes encoding FGF, nerve growth factor (NGF), brain-derived neurotrophic factor (BDNF), neurotrophin-3 (NT-3), neurotrophin-4 (NT-4), ciliary neurotrophic factor (CNTF), TGFβ, soluble TNF receptors, IL-10, IL-10 inhibites the, soluble Il-1 receptors, IL-1 receptor I, IL-1 receptor II, IL-1 receptor antagonist, and soluble IL-6 receptors.

Constructs according to the present invention preferably are applied or injected into damaged tissue, into an area of damaged nerves or into the spinal cord or into the brain to transduce endothelial cells or glial cells to express the therapeutic protein.

10. Therapeutic use

As an example, a construct as described in the above mentioned sections may be administered to a patient in need of treatment for a disease, for example a tumor, a leukemia, an inflammatory disorder, a disorder characterized by excess endothelial cell proliferation, a deficient production of blood cells, an autoimmune disease, an allergy, an impending rejection of a transplanted organ, an arthritis, an infection, a coagulation disorder or a CNS damage.

For administration, the construct described may be inserted into a plasmid vector or viral vector according to any of various techniques that are well known to the artisan. The vector may be applied to the patient locally or injected into the cardiovascular system, intrapleurally, intraperitoneally, intracerebrospinally, intravesically, intrabronchially, intragastrointestinally or injected into one of the different tissues or organs.

In case the gene of the construct codes for an enzyme that cleaves or transforms a nontoxic, noneffective prodrug into an effective drug, the prodrug is applied to the patient subsequent to the injection of the construct of this invention.

The present invention is explained in detail by means of the following examples which illustrate, but do not limit the scope of the invention.

EXAMPLES

1. Materials and Methods 1.1 Cell Culture, DNA Transfection, and Luciferase Assays NIH3T3 cells were cultured in Dulbecco-Vogt modified Eagle medium (DMEM) supplemented with 10% fetal calf serum, penicillin and streptomycin. HeLa cells were grown in DMEM plus 5% newborn calf serum. NIH3T3 cells were transfected by the DEAE dextran technique (Lucibello et al., EMBO J. 14, 132 (1995)). For synchronization in $G_0$, cells were maintained in serum free medium for 2 days 12 hrs. after transfection and restimulated with 10% FCS. Determination of luciferase activities and standardization of results using SV40 promoter-driven reporter constructs were performed as published (Lucibello et al., EMBO J. 14, 132 (1995)).

1.2 Sequence Analysis, Luciferase Constructs and Cell Cycle Regulation

The cdc25C and B-myb promoter-driven luciferase constructs have been described by Lucibello et al., EMBO J. 14, 132 (1995) and Zwicker et al., EMBO J. 14, 4514 (1995). Mutations were introduced by PCR strategies as previously described (Good and Nazar, Nucl. Acids Res. 20, 4934 (1992); Lucibello et al., EMBO J. 14, 132 (1995)). All PCR-amplified fragments were verified by DNA sequencing using the dideoxynucleotide chain-termination method using Sequenase (USB) or Tth polymerase (Pharmacia).

Cell cycle regulation was measured first by comparing the activity of wild-type and mutant constructs in quiescent NIH3T3 cells. See FIG. 2. The column in this Figure designated "repression" summarizes the results of this analysis. (+ratio: mutant wild-type: <2; –ratio mutant wild-type: >3. The functional promoter constructs were then analyzed for the timing of cell cycle regulation in serum-stimulated NIH3T3 cells and the times of half-maximal activities were determined. Hollow arrows indicate kinetics that clearly differ from both B-myb and cdc25C wild-type promoters. CDF-1 and E2F binding data were obtained by EMSA with wild-type and mutated B-myb E2FBS-CHR probes and with wild-type and mutated cdc25C CDE-CHR probes using HeLa cell nuclear extracts or partially purified CDF-1.

To demonstrate the effects of specific nucleotide changes on the timing of cell cycle-regulated transcription from the B-myb and cdc25C promoters, NIH3T3 cells were transiently transfected with the indicated constructs, synchronized in $G_0$ by serum deprivation and stimulated by adding 10% FCS. The data are based on 12 different experiments, except for the C-B1,2 graph which is based on 4 experiments. Data were normalized to 100 at 20 hrs. for each construct in order to facilitate a comparison of the half-maximal expression values.

1.3 EMSA

Electrophoretic mobility shift analysis (EMSA) was performed as described (Zwicker et al., Science 271, 1595 (1996)). When partially purified CDF-1 was used, the EMSA was carried out in the absence of sodium deoxycholate and NP-40. The following double-stranded probes were used:

cdc25C-wt:
  5'-ACTGGGCTGGCGGAAGGTTTGAATGGTCAA
  (SEQ ID NO.: 5) (CDE bold; CHR italic). T1, T4, T7
  (also referred to as cdc25C-mCDE), A8 and C9 are
  mutated (Zwicker et al., Nucleic Acids Res. 23, 3822,
  (1995)) at positions −19, −16, −13, −12 and −11 (FIG.
  1), respectively, as described.
cdc25C-10/−7:
  5'-ACTGGGCTGGCGGActtgTTGAATGGTCAA
  (SEQ ID NO.: 6)
cdc25C-6/−3 (also referred to as cdc25C-mCHR):
  5'-ACTGGGCTGGCGGAAGGTggtcATGGTCAA
  (SEQ ID NO.: 7)
cdc25C-1/+2:
  5'-ACTGGGCTGGCGGAAGGTTTGAAggtTCAA
  (SEQ ID NO.: 8)
cdc25C-2:
  5'-ACTGGGCTGGCGGAAGGTTTGAcTGGTCAA
  (SEQ ID NO.: 9).

The sequences of all other oligonucleotides, including B-myb, have been described elsewhere (Zwicker et al., Science 271, 1595 (1996)) or are indicated in FIG. 2. The random oligonucleotide contains an irrelevant sequence (Zwicker et al., EMBO J. 14, 4514 (1995)).

The following antibodies were used: E2F-1 (Santa Cruz SC-251X), E2F-2 (Santa Cruz SC-632X), E2F-3 (Santo Cruz SC-879X), E2F-4 (Santa Cruz SC-512X), E2F-5 (Santa Cruz SC-999X), DP-1 (obtained from N. La Thangue), DP-2 (Santa Cruz SC-830X).

1.4 Partial Purification of CDF-1

Nuclear extracts were prepared from HeLa suspension cultures in high salt extraction buffer (Dignam et al., Nucl. Acids Res. 11, 1475 (1983)) in the presence of the protease inhibitors leupeptin (50 ng/ml), pepstatin A (5 μg/ml) and aprotinin (80 ng/m.). A biotinylated oligonucleotide containing two tandem cdc25C CDE-CHR motifs was coupled to streptavidin agarose and used for affinity chromatography as described (Kadonaga and Tjian, PNAS 83, 5889 (1986)), using the same conditions as for EMSA (see above) except that salmon sperm DNA instead of Poly(dA:dT) used as the non-specific competitor. Elution was performed by step-wise increasing the KCl concentration to 1M.

1.5 In vitro DMS Footprinting

In vitro DMS footprinting of the coding strand cdc25C oligonucleotide was performed as described (Zwicker et al., Science 271, 1595 (1996)).

1.6 Genomic Footprinting of Stable Transfectants

For the generation of stable cell lines, the wild-type cdc25C luciferase construct C290 and the CHR mutant C290mCHR5/6 (TTTGAA mutated to TagGAA) were inserted into the pAGLu vector which contains a matrix attachment region (SAR), and introduced into NIH3T3 cells by electroporation. Stably transfected clones were isolated under G418 selection and analyzed for luciferase expression in quiescent and growing cells. Clones with the expected expression pattern were expanded and analyzed by genomic footprinting (Pfeifer et al., Science 246, 810 (1989)) as described (Lucibello et al., EMBO J. 14, 132 (1995)) with the exception that the first primer (P1) was specific for the luciferase gene 5'-GTAACACAAAGGAATTCAAGC (SEQ ID NO.: 10).

2. Results 2.1 Identification of CDF-1

2.1.1 Characterization of the cdc25C CHR

Recently, the consensus sequence of CDE was defined as G/CGC/TGG/C (GGCGG in cdc25C) (Zwicker al., EMBO J. 14, 4514 (1995)). For the CHR, however, such information is not yet available. In order to delineate the borders of the CHR and to identify critical nucleotide positions a number of mutations into the CHR of the cdc25C promoter were introduced and the function of these mutant constructs were analyzed by measuring their repression in NIH3T3 cells synchronized in G0. The data in FIG. 1 clearly show that the CHR extends from −7 to −2, and that all nucleotide positions in this region are essential. In contrast, the nucleotide positions between the CDE and the CHR (−11 to −8; AAGG) and the nucleotides downstream from the CHR (≧1; TGG . . . ) can be altered without detectable effects on repressor function. The cdc25C CHR can thus be defined as the sequence TTTGAA.

2.1.2 In vivo CDE Occupation is Dependent on an Intact CHR

Previous data have clearly shown that CDE and CHR when present in different promoters function in a synergistic way, since mutations in either element destroy repression in G0 (Zwicker al., EMBO J. 14, 4514 (1995)). This could mean that the interacting factor(s) bind cooperatively to both elements. This question was clarified by genomic footprinting of a stably transfected NIH3T3 cell line carrying a cdc25C promoter construct with an inactivating mutation in the CHR (cdc25C-mCHR5/6: TTTGAA changed to TagGAA). The expected protection pattern was observed in a control line stably expressing a wild-type cdc25C promoter construct. In contrast, the cell line harboring the cdc25C promoter with the CHR mutation did not show any protection in the region of the CDE and the mutated CHR, while occupation of two constitutive upstream binding sites for NF-Y (Lucibello et al., EMBO J. 14, 132 (1995)) was unchanged in the mutant promoter. Thus, it has to be concluded that CDE occupation is dependent on an intact CHR, indicating cooperative binding within the cell. This conclusion is supported by the observation that the insertion of either 5 bp or 10 bp between the CDE and the CHR in the cdc25C promoter abrogates repression.

2.1.3 Identification of CDF-1

Electrophoretic mobility shift analysis (EMSA) of HeLa cell nuclear extract led to the identification of an activity that interacts in a cooperative fashion with both the CDE and the CHR of the cdc25C promoter. In addition, binding of this activity to mutant repressor elements strongly correlated with the functional properties of these elements. Mutants (T for G at −19; C for A at −11; and deletion of −1/+2) exhibited a wild-type-like repressor function, and showed the same ability to compete in the binding assay as the wild-type sequence (self-competition). In contrast, other mutants in either the CDE (T for G in −16; T for G in −13 and A for G in −12) or the CHR (deletion of −10/−1, deletion of −6/−3 or C for A in −2) leading to a decreased or impaired repression in G0 cells, also showed a diminished ability to compete for binding. The observed cooperative binding taken together with the correlations established by the structure-function analysis are in agreement with the expected properties of the CDE-CHR binding factor. This activity was termed CDF-1.

2.1.4 CDF-1 Contacts the CDE in the Major Groove and CHR in the Minor Groove

In order to obtain additional evidence that CDF-1 is the activity interacting with repressor elements in vivo, the interaction of CDF-1 with DNA was analyzed by methylation protection footprinting in vitro. Previously it has been shown that in vivo, CDE contacts protein in its major groove, while CHR contacts protein in its minor groove (Zwicker et al., EMBO J. 14, 4514 (1995)). A very similar result was obtained by in vitro footprinting of the upper strand. The four G-residues in the CDE were specifically protected indicating major groove contacts (N-7). The two A-residues in the CHR were also specifically protected indicating minor groove contacts (N-3). The mode of interaction between CDF-1 and the CDE-CHR in vitro is thus fully compatible with the observations made intracellularly.

2.1.5 CDF-1 Interaction with Multiple Promoters Containing CDE-CHR Modules

Previous studies have shown that functional CDE-CHR modules are present in different promoters, including cdc25C, cdc2 and cyclin A (Zwicker et al., EMBO J. 14, 4514 (1995)). In addition, a similar configuration of binding sites is found in the B-myb promoter where an E2F site with a core sequence identical to the cdc25C CDE, is located immediately upstream of a CHR-like element (Bennett et al., Oncogene 13, 1073 (1996); Zwicker et al., Science 271, 1595 (1996)). It was therefore of obvious interest to investigate whether the CDF-1 activity identified above would interact with the repressor sites in these promoters. It could be found that both CDE-CHR containing promoters, i.e., cdc2 and cyclin A, bind the CDF-1 activity with a similar efficiency as the cdc25C promoter. In all three cases binding was dependent on a cooperative binding to both the CDE and CHR, since mutation (see Material and methods) in either site impaired competition with the cdc25C probe. At an identical ratio of probe: competitor (1:20), competition by the B-myb promoter E2FBS-CHR module was insignificant although some competition could be seen at higher competitor concentrations. The fact that the CDF-1 activity shows a specific and strong interaction with all three CDE-CHR containing promoters provides additional evidence for the relevance of the activity identified in the present study.

2.1.6 CDF-1 does not Contain a Known E2F Family Member

In view of the similarity of the CDE with an E2FBS it was sought to investigate whether the CDF-CHR activity identified above might contain known E2F or DP family members. For this purpose, EMSA was performed in the presence of antibodies directed against specific DP and E2F proteins. All of these antibodies have been shown to either induce supershifts or to extinguish binding of E2F/DP in different settings. However, it could clearly be shown that none of the antibodies used affected CDF1-DNA complex formation, indicating that CDF-1 does not contain any of the known E2F or DP family members.

2.2 Identification of Nucleotides, Determining Preferential E2F or CDF-1 or E2F and CDF-1 Binding The identification of nucleotide sequences binding E2F and CDF-1 was complicated by the fact that DP/E2F and CDF-1 complexes show very similar electrophoretic mobility in EMSA. Therefore HeLa nuclear extracts were fractionated by DNA-affinity chromatography using a 20 bp cdc25C CDE-CHR sequence (see Materials and methods for details). This procedure yielded partially purified CDF-1 showing very similar binding properties as the CDF-1 in crude extracts and gave a complete separation of CDF-1 from the E2F binding activity. For the analysis of E2F complexes cdc25C CDE-CHR competitor oligonucleotide was included in the binding reactions to prevent the formation of radiolabeled CDF-1 complexes.

To determine the binding sites of DP/E2F and CDF-1, specific nucleotides were swapped between the B-myb and cdc25C promoters in five specific regions where the repressor modules differ from each other (denoted 1–5 at the top of FIG. 2). The corresponding sequences were first tested for E2F binding (i.e., binding of DP1/E2F-1, -3 and -4 in HeLa nuclear extract) and interaction with partially purified CDF-1. This study yielded two clear results.

1. the nucleotides flanking the CDE or the core of the E2FBS (regions 1 and 2) play an important role in E2F binding. In contrast, the same residues do not noticeably influence CDF-1 binding. While the nucleotides in region 1 (CT in B-myb) influence the maximum binding of DP1/E2F-4 (B-C1 in FIG. 2), the G-residue in region 2 is crucial for the interaction with all E2F complexes (B-C,2 and B-C2 in FIG. 2). In agreement with this conclusion, the introduction of B-myb regions 1 and 2, but not region 1 alone, confers on the cdc25C CDE the ability to interact with DP1/E2F-1, -3 and -4 complexes with high efficiency (C-B1,2 in FIG. 2). In contrast, none of these nucleotide changes around the E2FBS core or the CDE affected the binding of CDF-1 (B-C1 and B-C1,2; B-C; C-B1 and C-B1,2 in FIG. 2).

2. The converse was true for CDF-1 binding: the structure of the CHR had a strong impact on CDF-1 binding while not influencing E2F binding, and in this respect region 4 was the crucial one. Thus, the exchange of two nucleotides in this region between cdc25C and B-myb led to a strong increase in CDF-1 binding to the B-myb promoter (B-C4 in FIG. 2), while the converse exchange destroyed binding of CDF-1 to the cdc25C promoter (C-B4 in FIG. 2). In contrast, the changes in the CHR in region 4 did not affect the binding of E2F complexes. Since it was formally possible that the Bmyb-CHR extended beyond the borders determined for the cdc25C CHR and the two promoters differ in these positions (regions 3 and 5 in the figure), it could not be excluded that C-B4 did not interact with CDF-1 due an incomplete Bmyb-CHR. Therefore the B-myb nucleotides found in regions 3 and 5 were also introduced into the cdc25C sequence in addition to the change in region 4 (C-B3,4, C-B3,4,5 and C-B4,5 in FIG. 2). However, these additional alterations could restore CDF-1 binding only to a marginal extent, confirming that the Bmyb-CHR and cdc25C-CHR sequences are not equivalent with respect to interacting proteins.

It was finally analyzed how the differential interaction of E2F and CDF-complexes with B-myb and cdc25C observed above would affect cell cycle regulated transcriptional repression and the timing of regulation. The same sequences tested for binding of E2F and CDF-1 were introduced into B-myb and cdc25C promoter luciferase constructs and tested for activity in serum stimulated NIH3T3 cells that had been synchronized in $G_0$. The data in FIG. 2 show that abrogation of E2F binding to the B-myb promoter in the presence of wild-type-like CDF-1 binding impairs repression in $G_0$ (see B-C1,2). This observation strongly indicates that E2F rather than CDF-1 complexes are responsible for cell cycle-regulated transcription of the B-myb gene which is in agreement with the relatively low affinity of CDF-1 for the B-myb promoter. In contrast it could be found that mutations in the cdc25C CDE which abrogate CDF-1 binding also impair cell cycle regulation. Likewise, replacement of the cdc25C with that of B-myb abolishes CDF-1 binding as well as repression in $G_0$ (C-B4; C-B3,4 and D-B3,4,5 in FIG. 2). The converse construct harboring a cdc25C CHR in a B-myb promoter background (B-C4) showed intermediate cell cycle kinetics, i.e., a delay in derepression of transcription relative to wild-type B-myb by 3 hrs.

2.3 Example for the Construction and use of a Gene Construct for Gene Therapy According to the Invention The selected gene construct has the following DNA components (listed downstream from 5' to 3'): the promoter/ early enhancer region of the SV40 (nucleotides 48 to 5191;

Tooze (ed.), DNA tumor Viruses (Cold Spring Harbor, New York, N.Y., Cold Spring Harbor Laboratory; Lucibello et al., EMBO J. 14, 132 (1995)) bound to SEQ ID NO.: 1 bound to sequence GCCACC (Kodak, J. Cell Biol., 108, 229 (1989)) bound to cDNA for the signal peptide of the immunoglobulin (nucleotide sequence ≦63 to ≧107; Riechmann et al., Nature 332, 323 (1988)) bound to cDNA for β-glucuronidase (nucleotide sequence ≦93 to ≧1982; Oshima et al., PNAS USA 84, 665 (1987)).

The gene construct is cloned into a pUC18/19 plasmid vector. The linkage of the different components of the gene construct is made via suitable sites that are preserved at the termini of each component via PCR amplification.

Moreover, ligases specific for the selected restriction sites are used. Those ligases are commercially available and known to the expert skilled in the art.

Cultured human umbilical cord endothelial cells (HuVEC) are transfected with the plasmids described above according to the method described by Lucibello et al. (EMBO J. 14, 132 (1995)).

The amount of β-glucuronidase, produced by the HuVECs, is measured by using 4-methylumbelliferyl-β-glucuronide as a substrate.

For testing cell cycle specificity, endothelial cells are synchronized in G0/G1 by methionin deprivation for 48 hours. The DNA content of the cells is measured by FACS analysis after staining with Hoechst 33258 (Lucibello et al., EMBO J. 14; 132 (1995)).

The following results can be achieved:

1. Transfected HuVECs secrete much more β-glucuronidase compared to nontransfected HuVECs.
2. Proliferating HuVECs (DNA>2S) secrete significantly more β-glucuronidase than HuVECs synchronized in G0/G1.
3. Accordingly, SEQ ID NO.: 1 leads to a cell cycle specific expression of β-glucuronidase in HuVECs transfected with a gene construct described above.

All cited publications are herein incorporated by reference in their entireties.

Priority application, European Patent Application No. 971025473, filed Feb. 18, 1997, including the specification, drawings, claims and abstract, is hereby incorporated by reference.

From the foregoing descriptions, one skilled in the art can easily ascertain the essential characteristics of this invention and, without departing from the spirit and scope thereof, can make various changes and modifications of the invention to adapt it to various usages and conditions.

What is claimed is:

1. A nucleic acid construct comprising:
   (a) at least one activator sequence;
   (b) at least one chimeric promoter module comprising a nucleotide sequence selected from the group consisiting of (SEQ ID NO: 1) ACTTGGCGGGAGATTTGAAT and (SEQ ID NO: 2) GCTTGGCGGGAGGTTTGAAT which binds a protein of the E2F family and binds a CDF-1 protein, wherein said activator sequence is upstream of said chimeric promoter module; and
   (c) at least one gene, wherein said chimeric promoter module promotes expression of said gene occurring later in a cell cycle than the regulation by a B-myb promoter but earlier than regulation by a cdc25C promoter.

2. The nucleic acid construct as claimed in claim 1, wherein said activator sequence is upstream of said chimeric promoter module.

3. The nucleic acid construct as claimed in claim 1, wherein said chimeric promoter module and said activator sequence cooperatively activate expression of said gene.

4. The nucleic acid construct as claimed in claim 1, wherein said activator sequence is cell-specific, metabolic-specific or virus-specific.

5. The nucleic acid construct as claimed in claim 4, wherein said cell-specific activator sequence is activated in a cell selected from the group consisting of an endothelial cell, a serosal cell, a smooth muscle cell, a muscle cell, a synovial cell, a macrophage, a lymphocyte, a leukemia cell, a tumor cell, a keratinocyte and a glial cell.

6. The nucleic acid construct as claimed in claim 4, wherein said virus-specific activator sequence is a promoter or enhancer sequence derived from a virus selected from the group consisting of HBV, HCV, HSV, HPV, EBV, HTLV, CMV, SV40 and HIV.

7. The nucleic acid construct as claimed in claim 1, wherein said gene encodes an enzyme or a fusion protein between a ligand and an enzyme which converts or cleaves a precursor of a pharmaceutically active molecule to produce said molecule.

8. The nucleic acid construct as claimed in claim 7, wherein said ligand is selected from the group consisting of a growth factor, a cytokine and an antibody protein.

9. The nucleic acid construct as claimed in claim 1, wherein said gene encodes a molecule which is selected from the group consisting of a cytokine, a growth factor, a cytokine receptor, a growth factor receptor, a protein having an antiproliferative effect, a protein having an apoptotic effect, a protein having a cytostatic effect, a protein having a cytotoxic effect, a protein having an inflammatory effect, a protein having an antiinflammatory effect, a protein having an immunosuppressive effect, an antibody, an antibody fragment, an angiogenesis inhibitor, a coagulation factor, a fibrinolytic compound, an anticoagulant, a blood protein, a viral antigen, a bacterial antigen, a tumor antigen, and a fusion protein between a ligand and one of the afore mentioned substances.

10. The nucleic acid construct as claimed in claim 1, which is DNA.

11. The nucleic acid construct as claimed in claim 1, comprising, in serial arrangement in a 5'-3' orientation:
   (a) nucleotides of the promoter/early enhancer region of SV40;
   (b) the sequence (SEQ ID NO: 1) ACCTTGGCGG-GAGATT;
   (c) nucleotides encoding a signal peptide of an immunoglobulin gene; and
   (d) nucleotides of the cDNA encoding β-glucuronidase.

12. A vector comprising the nucleic acid construct as claimed in claim 1.

13. A viral vector comprising the nucleic acid construct as claimed in claim 1.

14. A cell comprising at least one nucleic acid construct as claimed in claim 1.

15. A pharmaceutical composition comprising the nucleic acid of claim 1 and a pharmaceutically acceptable carrier, wherein at least one gene of said nucleic acid construct encodes an anti-tumor polypeptide.

16. A process for the preparation of a three-part nucleic acid construct, said nucleic acid construct comprising:
   (a) at least one activator sequence;
   (b) at least one chimeric promoter module comprising a nucleotide sequence selected from the group consisting of (SEQ ID NO: 1) ACTTGGCGGGAGATTTGAAT and (SEQ ID NO: 2) GCTTGGCGGGAGGTTTGAAT which binds a protein of the E2F family and binds a CDF-1 protein, wherein said activator sequence is upstream of said chimeric promoter module; and
   (c) at least one gene, wherein said chimeric promoter module promotes expression of said gene occurring later in a cell cycle than the regulation by a B-myb promoter but earlier than regulation by a cdc25C promoter;

said process comprising ligating parts (a), (b) and (c) together.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

ACTTGGCGGG AGATTTGAAT      20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

GCTTGGCGGG AGGTTTGAAT      20

(2) INFORMATION FOR SEQ ID NO: 3:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 3:

AGCAGGTGTT GGGAGGC                                                              17

(2) INFORMATION FOR SEQ ID NO: 4:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GGCCGATGGG CAGATAGAGG GGGCCGATGG GCAGATAGAG G                                    41

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

ACTGGGCTGG CGGAAGGTTT GAATGGTCAA                                                 30

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

ACTGGGCTGG CGGACTTGTT GAATGGTCAA                                                 30

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

ACTGGGCTGG CGGAAGGTGG TCATGGTCAA                                                 30

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

ACTGGGCTGG CGGAAGGTTT GAAGGTTCAA                                                 30

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

ACTGGGCTGG CGGAAGGTTT GACTGGTCAA        30

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GTAACACAAA GGAATTCAAG C        21

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GGCTGGCGGA AGGTTTGAAT        20

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GGCTGGCGGA AGGTTTGAAT GGCTGGCGGA AGGTTTGAAT        40

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

ACTTGGCGGG AGATAGGAAA        20

(2) INFORMATION FOR SEQ ID NO: 14:

-continued

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GGCGGAAGGT TTGAATGG                                              18

(2) INFORMATION FOR SEQ ID NO: 15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

ACTTGGCGGG AGATAGGAAA GT                                         22

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GGCTGGCGGA AGGTTTGAAT GG                                         22
```